United States Patent
Peglion et al.

(10) Patent No.: US 6,696,469 B2
(45) Date of Patent: Feb. 24, 2004

(54) CYCLOBUTENEDIONE COMPOUNDS

(75) Inventors: Jean-Louis Peglion, Le Vesinet (FR); Jean-Paul Vilaine, Chatenay Malabry (FR); Nicole Villeneuve, Rueil Malmaison (FR); Catherine Thollon, Paris (FR); Marie-Pierre Bourguignon, Chatou (FR); Christophe Poitevin, Paris (FR)

(73) Assignee: Les Laboratoires Servier, Neuilly-sur-Seine (FR)

( * ) Notice: Subject to any disclaimer, the term of this patent is extended or adjusted under 35 U.S.C. 154(b) by 0 days.

(21) Appl. No.: 09/976,572

(22) Filed: Oct. 12, 2001

(65) Prior Publication Data

US 2002/0065419 A1 May 30, 2002

(30) Foreign Application Priority Data

Oct. 12, 2000 (FR) .............................. 00 13072

(51) Int. Cl.$^7$ .................... A61K 31/445; C07D 401/12
(52) U.S. Cl. ................. 514/331; 514/317; 514/300; 514/320; 514/322; 514/323; 546/113; 546/196; 546/199; 546/201; 546/229; 546/236
(58) Field of Search ................ 514/317, 300, 514/320, 322, 323, 331; 546/113, 196, 199, 201, 229, 236

(56) References Cited

U.S. PATENT DOCUMENTS 6,432,960 B2 * 8/2002 Sit et al. ................ 514/253.13

OTHER PUBLICATIONS

Langham et al. "Preparation of . . . " CA 134:29705 (2000).*
Takeno et al. "Preparationof 1,2–diaminocyclogutene . . . " CA 121:133584 (1994).*
DeFily "Preconditioning protects coromary endothelium . . . " CA 119:223195 (1993).*
De Clerck "Pathological expressions of . . . " Ca 117:67498 (1992).*
R. Candipan, et al., Regression or Progression: Dependency on Vascular Nitric Oxide, *Arterioscler Thromb Vasc Biol* 1996; 16:44–50.
J. Cooke, et al., Antiatherogenic Effects of L–Arginine in the Hypercholesterolemic Rabbit, *J Clin Invest* 1992; 90:1168–1172.
G. Dillon, et al., Nitric Oxide and Endothelial Dysfunction, *Contemporary Cardiology*, vol. 4, Chap 13, Humana Press Inc., Totowa, NJ.
R. Eberhardt, et al., Nitric Oxide in Atheroscleorosis, *Contemporary Cardiology*, vol. 4, Chap 16, Humana Press Inc., Totowa, NJ.
K. Kauser, et al., Role of Endogeneous Nitric Oxide in Progression of Atherosclerosis in Apolipoprotein E–Deficient Mice, *Am J Physiol Heart Circ Physiol*, 2000; 278:H1679–H1685.
P. Ludmer, et al., Paradoxical Vasoconstriction Induced by Acetylcholine in Atherosclerotic Coronary Arteries, *N Engl J Med* 1986; 315:1046–1051.
C. Napoli, et al., Nitric Oxide and Atherosclerosis, *NITRIC OXIDE:Biology and Chemistry*, vol. 5, pp 88–97 (2001).
K. Naruse, et al., Long–term Inhibition of NO Synthesis Promotes Atherosclerosis in the Hypercholesterolemic Rabbit Thoracic Aorta, *Arterioscler Thromb* 1994;14:746–752.
V. Schachinger, et al., Prognostic Implications of Endothelial Dysfunction: Does It Mean Anything? *Coronary Artery Dis* 2001; 12:435–443.
B. Wang, et al., Dietary Arginine Prevents Atherogenesis in the Coronary Artery of the Hypercholesterolemic Rabbit, *J Am Coll Cardiol* 1994; 23:452–458.
A. Zeiher, et al., Modulation of Coronary Vasomotor Tone in Humans, *Circulation* 1991; 83:391–401.

* cited by examiner

Primary Examiner—Ceila Chang
(74) Attorney, Agent, or Firm—The Firm of Hueschen and Sage

(57) ABSTRACT

Compounds of formula (I):

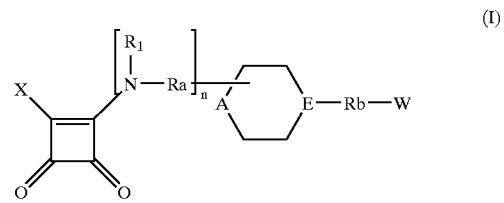

wherein:
  X represents a heterocycle bonded to the remainder of the molecule by a nitrogen atom of the heterocycle, or an —NR$_2$R$_3$ group wherein R$_2$ represents hydrogen or alkyl, and R$_3$ represents aryl, 1,3 dihydro-2H-benzimidazolyl-2-one or alkyl substituted by a heterocycle,
  n represents zero or 1,
  R$_1$ represents hydrogen or alkyl,
  Ra represents a single bond or an alkylene chain,
  A represents nitrogen or CH,
  E represents nitrogen or CRe, wherein Re is as defined in the description,
  Rb represents a single bond or an alkylene chain as defined in the description,
  W represents aryl or heteroaryl, Their optical isomers, and addition salts thereof with a pharmaceutically acceptable acid, and
  medicinal products containing the same which are useful for treatment of diseases or pathological conditions in which endothelial dysfunction is known.

16 Claims, No Drawings

CYCLOBUTENEDIONE COMPOUNDS

BACKGROUND OF THE INVENTION

The compounds of the present invention are useful in the treatment of diseases or pathological conditions in which endothelial dysfunction is known to be a pathogenic and/or aggravating mechanism. Such pathologies are: atherosclerosis, the existence of vascular risk factors (dyslipidaemia, diabetes, systemic arterial hypertension), the various clinical forms of myocardial or peripheral ischaemia, cardiac insufficiency and the various forms of pulmonary arterial hypertension. The said compounds are also useful in the treatment of patients undergoing heart transplantation or vascular repermeabilisation, such as a bypass, thrombolysis or arterial dilatation with or without a stent.

A reduction in the vascular availability of nitrogen monoxide (NO) constitutes the major mechanism of endothelial dysfunction observed in the diseases and pathological conditions mentioned above and explains its pathogenic role (*Cardiovasc. Res.*, 1999, 43, 572; *Coronary. Art. Dis.* 1999, 10 277; *Coronary. Art. Dis.*, 1999, 10, 301; *Coronary. Art. Dis.*, 1999, 10, 287; *Coronary. Art. Dis.*, 1999, 10, 295).

In the said pathological conditions, the endothelial dysfunction may in fact result from two main mechanisms: 1) inadequate production of NO associated with inhibition of endothelial NO synthase by endogenous inhibitors, such as ADMA (asymmetric dimethyl-arginine), the plasma concentration of which increases in patients exhibiting cardiovascular risk factors (*Cardiovasc. Res.*, 1999, 43, 542; *Hypertension*, 1997, 29, 242; *Circulation*, 1997, 95, 2068), 2) inactivation of the NO by the superoxide anion ($O_2^-$), the production of which is increased in pathological conditions (*Cardiovasc. Res.*, 1999, 43, 562; *Eur.J Biochem.* 1997, 245, 541; *J. Clin. Invest.*, 1993, 91 2546).

Under normal conditions, NO produces major effects such as: 1) regulation of arterial vasomotricity by means of its vasodilator effect (*N Engl. J Med.*, 1993, 329, 2002; *Nature*, 1980, 288, 373), 2) limitation of platelet adhesion and aggregation (*Trends Pharmacol. Sci.*, 1991, 12, 87), 3) control of the adhesion of leukocytes and monocytes to endothelial cells (*Proc. Natl Acad. Sci. USA*, 1991, 88, 4651), 4) inhibition of the proliferation of vascular smooth muscle cells (*Cardiovasc. Res.*, 1999, 43, 580, *Circulation*, 1993, 87 V51), which explains why the deficiency of NO in the arterial wall is favourable to pathological phenomena, such as vasoconstriction, thrombosis, lipid accumulation and proliferation of vascular smooth muscle cells.

In vitro experiments have enabled it to be shown that the compounds of the present invention are capable of limiting the endothelial dysfunction and reduced vascular availability of NO that were induced by tests involving the two physiopathological mechanisms already mentioned: inhibition of endothelial NO synthase and oxidative stress due to production of $O_2^-$.

Besides the fact that they are new, the compounds of the present invention, by virtue of their specific pharmacological activity, which is capable of limiting the development of endothelial dysfunction, are useful in preventing the development, extension and complications of atherosclerotic lesions, especially in patients exhibiting a vascular risk factor (dyslipidaemia, diabetes, arterial hypertension), and in treating the various clinical forms of myocardial or peripheral ischaemia, cardiac insufficiency and the various forms of pulmonary arterial hypertension. The compounds are also used for preventing vascular complications (spasm, thrombosis, restenosis, accelerated atherosclerosis) in patients undergoing a bypass, vascular dilatation with or without a stent or other forms of vascular repermeabilisation and also heart transplantation.

DETAILED DESCRIPTION OF THE INVENTION

More specifically, the present invention relates to compounds of formula (I):

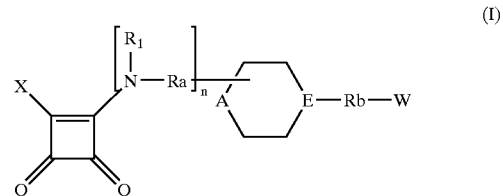

wherein:
X represents:
a monocyclic or bicyclic, saturated, partially unsaturated or aromatic heterocycle, having from 5 to 12 ring members, containing from 1 to 3 hetero atoms selected from oxygen, nitrogen and sulphur but containing at least one nitrogen atom, said heterocycle being bonded to the remainder of the molecule by said nitrogen atom, and said heterocycle being optionally substituted,
or a group of formula —$NR_2R_3$ wherein $R_2$ represents a hydrogen atom or a linear or branched ($C_1$–$C_6$)alkyl group, and $R_3$ represents an aryl group optionally substituted, a 1,3-dihydro-2H-benzimidazolyl-2-one group, or a linear or branched ($C_1$–$C_6$)alkyl group substituted by a monocyclic or bicyclic, saturated, partially unsaturated or aromatic heterocycle, having from 5 to 12 ring members, containing from 1 to 3 hetero atoms selected from oxygen, nitrogen and sulphur but containing at least one nitrogen atom, said heterocycle being optionally substituted,
n in represents zero or 1,
$R_1$ represents a hydrogen atom or a linear or branched ($C_1$–$C_6$)alkyl group,
Ra represents a single bond or a linear or branched ($C_1$–$C_6$)alkylene chain,
A represents a nitrogen atom or a CH group, but A represents only a CH group when Ra represents a single bond, and A represents only a nitrogen atom when n represents zero,
E represents a nitrogen atom or a CRe group wherein Re represents either a hydrogen atom, or a bond to a carbon atom of W, it being understood that at least one of the groups A and E represents a nitrogen atom,
Rb represents a single bond or a linear or branched ($C_1$–$C_6$)alkylene chain, one of the carbon atoms of which is optionally replaced by an oxygen atom or a sulphur atom,
W represents an aryl or heteroaryl group, each of those groups being optionally substituted,
their optical isomers, their hydrates, their solvates and addition salts thereof with a pharmaceutically acceptable acid, it being understood that:
"aryl group" is understood to mean a group selected from phenyl, biphenyl, bicyclo[4.2.0]octa-1,3,5-trienyl, naphthyl, dihydronaphthyl, tetrahydronaphthyl, indanyl and indenyl, "heteroaryl group" is understood to mean an aryl group as defined above containing from 1 to 3 identical or different hetero atoms selected from oxygen, nitrogen and sulphur, "optionally substituted", when associated with "heterocycle", "aryl group" or "heteroaryl group", is understood to mean optionally substituted by one or more identical or different groups selected from halogen, linear or branched ($C_1$–$C_6$)alkyl, hydroxy, linear or branched ($C_1$–$C_6$)alkoxy, mercapto, linear or branched ($C_1$–$C_6$)alkylthio, linear or branched ($C_1$–$C_6$) trihaloalkyl, cyano, nitro, amino, linear or branched ($C_1$–$C_6$)-alkylamino, dialkylamino in which each alkyl moiety has from 1 to 6 carbon atoms and is linear or branched, and methylenedioxy, "optical isomers" are understood to mean the enantiomers and diastereoisomers.

Among the pharmaceutically acceptable acids, there may be mentioned by way of non-limiting example hydrochloric acid, hydrobromic acid, sulphuric acid, phosphoric acid, acetic acid, trifluoroacetic acid, lactic acid, pyruvic acid, malonic acid, succinic acid, glutaric acid, fumaric acid, tartaric acid, maleic acid, citric acid, ascorbic acid, oxalic acid, methanesulphonic acid, camphoric acid.

The compounds of the invention are preferably the compounds of formula (IA):

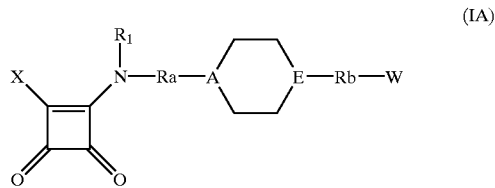

(IA)

wherein X, $R_1$, Ra, A, E, Rb and W are as defined for formula (I).

According to an advantageous embodiment of the invention, the preferred compounds are the compounds of formula (I) wherein X represents a heterocycle as defined for formula (I).

According to another advantageous embodiment, the preferred compounds of the invention are the compounds of formula (I) wherein X represents a group of formula —$NR_2R_3$ as defined for formula (I).

Especially advantageously, the preferred compounds of the invention are the compounds of formula (I) wherein X represents a 1-indolinyl or 2,3-dihydro-1H-pyrrolo[2,3-c] pyridin-1-yl group, each of those groups being optionally substituted by one or more groups as defined for formula (I).

Also especially advantageously, the preferred compounds of the invention are the compounds of formula (I) wherein X represents a group of formula —$NR_2R_3$ wherein $R_2$ represents a hydrogen atom and $R_3$ represents an optionally substituted phenyl group.

According to an embodiment of the invention of interest, the preferred compounds of the invention are the compounds of formula (I) wherein W represents a heteroaryl group, and advantageously W represents a benzofuryl or indolyl group.

According to another embodiment of the invention of interest, the preferred compounds of the invention are the compounds of formula (I) wherein —Rb—W together form an aryloxyalkyl group in which the alkyl moiety has from 1 to 5 carbon atoms and is linear or branched and the aryl moiety is optionally substituted.

The preferred compounds of the invention are:

3-anilino-4-({2-[4-(phenoxymethyl)-1-piperidinyl] ethyl}amino)-3-cyclobutene-1,2-dione and its methanesulphonate, 3-(4-chloroanilino)-4-({2-[4-(phenoxymethyl)-1-piperidinyl]ethyl}amino)-3cyclobutene-1,2-dione and its methanesulphonate, 3-(2,3-dihydro-1H-indol-1-yl)-4-({2-[4-(phenoxymethyl)-1-piperidinyl]ethyl}amino)-3-cyclobutene-1,2-dione and its methanesulphonate, 3-({1-[2-(1-benzofuran-3-yl)ethyl]-4-piperidinyl}amino)-4-(4-fluoroanilino)-3-cyclobutene-1,2-dione and its methanesulphonate, 4-{[2-({1-[2-(1-benzofuran-3-yl)ethyl]-4-piperidinyl}amino)-3,4-dioxo-1-cyclobutene-1-yl] amino}benzonitrile and its methanesulphonate, 3-[(2-{4-[2-(4-fluorophenoxy)ethyl]-1-piperidinyl}ethyl) amino]-4-[(2-oxo-2,3-dihydro-1H-benzimidazol-5-yl) amino]-3-cyclobutene-1,2-dione and its methanesulphonate 3-(5-methoxy-2,3-dihydro-1H-pyrrolo[2,3-c]pyridin-1-yl)-4-({2-[4-(phenoxymethyl)-1-piperidinyl]ethyl}amino)-3-cyclobutene-1,2-dione and its dihydrochloride, 3-[(2-{4-[2-(4-fluorophenoxy)ethyl]-1-piperidinyl}ethyl) amino]-4-(5-methoxy-2,3-dihydro-1H-pyrrolo[2,3-c] pyridin-1-yl)-3-cyclobutene-1,2-dione and its dihydrochloride 3-[(2-{4-[2-(4-fluorophenoxy)ethyl]-1-piperidinyl}ethyl) amino]-4-(4,5,6-trimethoxy-2,3-dihydro-1H-indol-1-yl)-3-cyclobutene-1,2-dione and its methanesulphonate, 3-(6-chloro-2,3-dihydro-1H-indol-1-yl)-4-[(2-{4-[2-(4-fluorophenoxy)-ethyl]-1-piperidinyl}ethyl)amino]-3-cyclobutene-1,2-dione and its methanesulphonate, 3-(2,3-dihydro-1H-indol-1-yl)-4-[({1-[2-(1H-indol-3-yl) ethyl]-3-piperidinyl}methyl)amino]-3-cyclobutene-1,2-dione and its hydrochloride, 3-(5,6-dimethoxy-2,3-dihydro-1H-indol-1-yl)-4-[(2-{4-[2-(4-fluoro-phenoxy)ethyl]1-piperidinyl}ethyl)amino]-3-cyclobutene-1,2-dione and its methanesulphonate, 3-[(2-{4-[2-(4-fluorophenoxy)ethyl]-1-piperidinyl}ethyl) amino]-4-(6-methoxy-2,3-dihydro-1H-indol-1-yl)-3-cyclobutene-1,2-dione and its methanesulphonate, and 3-(4,5-dimethoxy-2,3-dihydro-1H-indol-1-yl)-4-[(2-{4-[2-(4-fluoro-phenoxy)ethyl]-1-piperidinyl}ethyl)amino]-3-cyclobutene-1,2-dione and its methanesulphonate.

The isomers, hydrates, solvates and addition salts with a pharmaceutically acceptable acid of the preferred compounds of the invention form an integral part of the invention.

The present invention relates also to a process for the preparation of compounds of formula(I), characterised in that there is used as starting material a compound of formula (II):

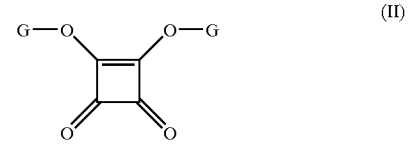

(II)

wherein G represents a linear or branched ($C_1$–$C_4$)alkyl group, which compound of formula (II) is reacted with an amine of formula (III):

X—H  (III)

wherein X is as defined for formula (I),
to yield a compound of formula (IV):

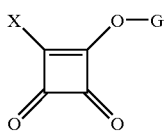

wherein X and G are as defined hereinbefore,
which compound of formula (IV) is treated with a compound of formula (V):

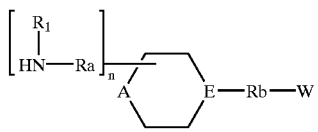

wherein n, $R_1$, Ra, Rb, A, E and W are as defined for formula (I),
to yield compounds of formula (I) as defined:

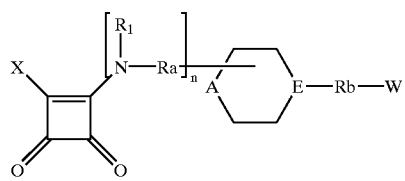

which compounds of formula (I) are purified, if necessary, according to a conventional purification technique, may, if desired, be separated into their different isomers according to a conventional separation technique, and are converted, if desired, into addition salts thereof with a pharmaceutically acceptable acid.

The compounds of formulae (II), (III) and (V) are either commercial products or are obtained according to conventional methods of organic synthesis.

The compounds of the present invention are useful in the treatment of diseases or pathological conditions in which endothelial dysfunction is known. Accordingly, by virtue of their specific pharmacological activity the compounds of the invention are useful in preventing the development, extension and complications of atherosclerotic lesions, in the treatment of myocardial or peripheral ischaemia, cardiac insufficiency, pulmonary arterial hypertension, and in the prevention of vascular complications after vascular bypass, vascular dilatation, vascular repermeabilisation and heart transplantation.

The present invention relates also to pharmaceutical compositions comprising as active ingredient at least one compound of formula (I), an optical isomer, hydrate or solvate or an addition salt thereof with a pharmaceutically acceptable acid, in combination with one or more inert, non-toxic, pharmaceutically acceptable excipients or carriers.

Among the pharmaceutical compositions according to the invention, there may be mentioned more especially those that are suitable for oral, parenteral (intravenous, intramuscular or subcutaneous), per- or trans-cutaneous, nasal, rectal, perlingual, ocular or respiratory administration, and especially tablets or dragées, sublingual tablets, soft gelatin capsules, hard gelatin capsules, suppositories, creams, ointments, dermal gels, injectable or drinkable preparations, aerosols, eye or nose drops.

The useful dosage varies according to the age and weight of the patient, the route of administration, the nature and severity of the disorder, and whether any associated treatments are being taken, and ranges from 1 mg to 200 mg per day in one or more administrations.

The following Examples illustrate the invention but do not limit it in any way. The starting materials used are known products or are prepared according to known procedures. The various preparations yield synthesis intermediates for use in the preparation of the compounds of the invention.

The structures of the compounds described in the Examples were determined according to the usual spectrophotometric techniques (infrared, nuclear magnetic resonance, mass spectrometry, etc.).

The melting points were determined using a Kofler hot-plate (K.) or a hotplate under a microscope (M.K.).

EXAMPLE 1

3-Anilino-4-({2-[4-(phenoxymethyl)-1-piperidinyl]ethyl}amino)-3-cyclobutene-1,2-dione and its methanesulphonate Step 1: 4-Anilino-3-ethoxy-3-cyclobutene-1,2-dione 0.01 mol of aniline is added to a solution of 0.01 mol of 3,4-diethoxy-3-cyclobutene-1,2-dione in 30 ml of anhydrous ethanol. The mixture is refluxed for 12 hours and the precipitate that forms is filtered off while hot. The resulting residue is solidified in the presence of ether enabling the expected product to be isolated.

Melting point (K): 110° C.

Step 2: 3-Anilino-4-({2-[4-(phenoxymethyl)-1-piperidinyl]ethyl}amino)-3-cyclobutene-1,2-dione and its methanesulphonate 0.01 mol of the product obtained in Step 1 and 0.01 mol of 2-[4-(phenoxymethyl)-1-piperidinyl]ethylamine in 66 ml of anhydrous ethanol are refluxed for 18 hours. The resulting precipitate is filtered off while hot and dried to yield the expected product, which is converted to its methanesulphonate salt by the action of a solution of 1.5 equivalents of methanesulphonic acid in methanol at reflux for 2 hours.

Melting point (M.K.): 258–262° C.

EXAMPLE 2

3-(4-Fluoroanilino)-4-({2-[4-(phenoxymethyl)-1-piperidinyl]-ethyl}amino)-3-cyclobutene-1,2-dione and its methanesulphonate Step 1: 3-Ethoxy-4-(4-fluoroanilino)-3-cyclobutene-1,2-dione The product is obtained according to the process described in Step 1 of Example 1 using p-fluoroaniline instead of aniline.

Melting point (K): 180° C.

Step 2: 3-(4-Fluoroanilino)-4-({2-[4-(phenoxymethyl)-1-piperidinyl]ethyl}amino)-3-cyclobutene-1,2-dione and its methanesulphonate The product is obtained according to the process described in Step 2 of Example 1 using the compound described in the preceding Step.

Melting point (M.K.): 218–221° C.

EXAMPLE 3

3-(4-Chloroanilino)-4-({2-[4-(phenoxymethyl)-1-piperidinyl]-ethyl}amino)-3-cyclobutene-1,2-dione and its methanesulphonate Step 1: 4-(4-Chloroanilino)-3-ethoxy-3-cyclobutene-1,2-dione The product is obtained according to the process described in Step 1 of Example 1 using p-chloroaniline instead of aniline.

Melting point (K): 149° C.

Step 2: 3-(4-Chloroanilino)-4-({2-[4-(phenoxymethyl)-1-piperidinyl]ethyl}amino)-3-cyclobutene-1,2-dione and its methanesulphonate The product is obtained according to the process described in Step 2 of Example 1 using the compound described in the preceding Step.

Melting point (M.K.): 243–246° C.

EXAMPLE 4

4-{[3,4-Dioxo-2-({2-[4-(phenoxymethyl)-1-piperidinyl]ethyl}amino)-1-cyclobuten-1-yl]amino}benzonitrile and its methanesulphonate Step 1: 4-(4-Cyanoanilino)-3-ethoxy-3-cyclobutene-1,2-dione The product is obtained according to the process described in Step 1 of Example 1 using p-cyanoaniline instead of aniline.

Melting point (K): 230° C.

Step 2: 4-{[3,4-Dioxo-2-({2-[4-phenoxymethyl)-1-piperidinyl]ethyl}amino)-1-cyclobuten-1-yl]amino}benzonitrile and its methanesulphonate The product is obtained according to the process described in Step 2 of Example 1 using the compound described in the preceding Step.

Melting point (M.K.) 295–299° C.

EXAMPLE 5

3-(2,3-Dihydro-1H-indol-1-yl)-4-({2-[4-(phenoxymethyl)-1-piperidinyl]-ethyl}amino)-3-cyclobutene-1,2-dione and its methanesulphonate Step 1: 3-Ethoxy-4-(indolin-1-yl)-3-cyclobutene-1,2-dione The product is obtained according to the process described in Step 1 of Example 1 using indoline instead of aniline.

Melting point (K): 204° C.

Step 2: 3-(2,3-Dihydro-1H-indol-1-yl)-4-({2-[4-(phenoxymethyl)-1-piperidinyl]-ethyl}amino)-3-cyclobutene-1,2-dione and its methanesulphonate The product is obtained according to the process described in Step 2 of Example 1 using the compound described in the preceding Step.

Melting point (M.K.): 209–213° C.

EXAMPLE 6

3-Anilino-4-({1-[2-(1-benzofuran-3-yl)ethyl]-4-piperidinyl}amino)-3-cyclobutene-1,2-dione and its methanesulphonate The product is obtained according to the process of Step 2 of Example 1 but using as substrate the product of Step 1 of Example 1 and 1-[2-(1-benzofuran-3-yl)ethyl]4-piperidinylamine.

Melting point (M.K) 276–280° C.

EXAMPLE 7

3-({1-[2-(1-Benzofuran-3-yl)ethyl]-4-piperidinyl}amino)-4-(4-fluoroanilino)-3-cyclobutene-1,2-dione and its methanesulphonate The product is obtained according to the process of Example 6 using the product of Step 1 of Example 2 instead of the product of Step 1 of Example 1.

Melting point (M.K.): 266–271° C.

EXAMPLE 8

3-({1-[2-(1-Benzofuran-3-yl)ethyl]-4-piperidinyl}amino)-4-(4-chloroanilino)-3-cylobutene-1,2-dione and its methanesulphonate The product is obtained according to the process of Example 6 using the product of Step 1 of Example 3 instead of the product of Step 1 of Example 1.

Melting point (M.K): 283–287° C.

EXAMPLE 9

4-{[2-({1-[2-(1-Benzofuran-3-yl)ethyl]-4-piperidinyl}amino)-3,4-dioxo-1-cyclobuten-1-yl]amino}benzonitrile and its methanesulphonate The product is obtained according to the process of Example 6 using the product of Step 1 of Example 4 instead of the product of Step 1 of Example 1.

Melting point (M.K.) 295–299° C.

EXAMPLE 10

3-({1-[2-(1-Benzofuran-3-yl)ethyl]-4-piperidinyl}amino)-4-2,3-dihydro-1H-indol-1-yl)-3-cyclobutene-1,2-dione and its methanesulphonate The product is obtained according to the process of Example 6 using the product of Step 1 of Example 5 instead of the product of Step 1 of Example 1.

Melting point (M.K.): 265–270° C.

EXAMPLE 11

3-(4-Chloroanilino)-4-[(2-{4-[2-(4-fluorophenoxy)ethyl]-1-piperidinyl}-ethyl)amino]-3-cyclobutene-1,2-dione and its methanesulphonate The product is obtained according to the process of Example 1 using p-chloroaniline as substrate in Step 1 and 2-{4-[2-(4-fluorophenoxy)ethyl]-1-piperidinyl}ethylamine as substrate in Step 2.

Melting point: 215–219° C.

EXAMPLE 12

3-[(2-{4-[2-(4-Fluorophenoxy)ethyl]-1-piperidinyl}ethyl)amino]-4-(4-nitroanilino)-3-cyclobutene-1,2-dione and its methanesulphonate The product is obtained according to the process of Example 1 using p-nitroaniline as substrate in Step 1 and 2-{4-[2-(4-fluorophenoxy)ethyl]-1-piperidinyl}ethylamine as substrate in Step 2.

Melting point: 223–227° C.

EXAMPLE 13

3-[(2-{4-[2-(4-Fluorophenoxy)ethyl]-1-piperidinyl}ethyl)amino]-4-(5-nitro-2,3-dihydro-1H-indol-1-yl)-3-cyclobutene-1,2-dione and its methanesulphonate The product is obtained according to the process of Example 1 using 5-nitroindoline as substrate in Step 1 and 2-{4-[2-(4-fluorophenoxy)ethyl]-1-piperidinyl}ethylamine as substrate in Step 2.

Melting point: 232–235° C.

EXAMPLE 14

3-[(2-Oxo-2,3-dihydro-1H-benzimidazol-5-yl)
amino]-4-({2-[4-(phenoxy-methyl)-1-piperidinyl]
ethyl}amino)-3-cyclobutene-1,2-dione and its
methanesulphonate The product is obtained according to the process of
Example 1 using 5-amino-1,3-dihydro-2H-benzimidazol-2-one as substrate in Step 1.

Melting point: 176–180° C.

EXAMPLE 15

3-[({4-[2-(4-Fluorophenoxy)ethyl]-1-
piperidinyl}ethyl)amino]-4-[(2-oxo-2,3-dihydro-1H-
benzimidazol-5-yl)amino]-3-cyclobutene-1,2-dione
and its methanesulphonate The product is obtained according to the process of
Example 1 using 5-amino-1,3-dihydro-2H-benzimidazol-2-one as substrate in Step 1 and 2-{4-[2-(4-fluorophenoxy)
ethyl]-1-piperidinyl}ethylamine as substrate in Step 2.

Melting point: 184–188° C.

EXAMPLE 16

3-(6,7-Dihydro-5H-[1,3]dioxolo[4,5-f]indol-5-yl)-4-
({2-[4-(phenoxy-methyl)-1-piperidinyl]
ethyl}amino)-3-cyclobutene-1,2-dione and its
methanesulphonate The product is obtained according to the process of
Example 1 using 6,7-dihydro-5H-[1,3]dioxolo[4,5-f]indole
as substrate in Step 1.

Melting point: 193–196° C.

EXAMPLE 17

3-(5-Methoxy-2,3-dihydro-1H-pyrrolo[2,3-c]
pyridin-1-yl)-4-({2-[4-(phenoxymethyl)-1-
piperidinyl]ethyl}amino)-3-cyclobutene-1,2-dione
and its dihydrochloride The product is obtained according to the process of
Example 1 using 5-methoxy-2,3-dihydro-1H-pyrrolo[2,3-c]
pyridine as substrate in Step 1.

Melting point: 190–195° C.

EXAMPLE 18

3-[(2-{4-[2-(4-Fluorophenoxy)ethyl]-1-
piperidinyl}ethyl)amino]-4-(5-methoxy-2,3-dihydro-
1H-pyrrolo[2,3-c]pyridin-1-yl)-3-cyclobutene-1,2-
dione and its dihydrochloride The product is obtained according to the process of
Example 1 using 5-methoxy-2,3-dihydro-1H-pyrrolo[2,3-c]
pyridine as substrate in Step 1 and 2-{4-[2-(4-fluoro-
phenoxy)ethyl]-1-piperidinyl}ethylamine as substrate in
Step 2.

Melting point: 224–228° C.

EXAMPLE 19

3-(5-Fluoro-2,3-dihydro-1H-indol-1-yl)-4-[(2-{4-[2-
(4-fluorophenoxy)-ethyl]-1-piperidinyl}ethyl)
amino]-3-cyclobutene-1,2-dione and its
methanesulphonate The product is obtained according to the process of
Example 1 using 5-fluoroindoline as substrate in Step 1 and
2-{4-[2-(4-fluorophenoxy)ethyl]-1-piperidinyl}ethylamine
as substrate in Step 2.

Melting point: 166–170° C.

EXAMPLE 20

3-[(2-{4-[2-(4-Fluorophenoxy)ethyl]-1-
piperidinyl}ethyl)amino]-4-(4,5,6-trimethoxy-2,3-
dihydro-1H-indol-1-yl)-3-cyclobutene-1,2-dione and
its methanesulphonate The product is obtained according to the process of
Example 1 using 4,5,6-trimethoxy-indoline as substrate in
Step 1 and 2-{4-[2-(4-fluorophenoxy)ethyl]-1-piperidinyl}-
ethylamine as substrate in Step 2.

Melting point: 176–180° C.

EXAMPLE 21

3-(2,3-Dihydro-1H-indol-1-yl)-4-[(2-{4-[2-(4-
fluorophenoxy)ethyl]-1-piperidinyl}ethyl)amino]-3-
cyclobutene-1,2-dione and its methanesulphonate The product is obtained according to the process of
Example 1 using indoline as substrate in Step 1 and 2-{4-
[2-(4-fluorophenoxy)ethyl]-1-piperidinyl}ethylamine as
substrate in Step 2.

Melting point: 182–186° C.

EXAMPLE 22

3-(6Chloro-2,3-dihydro-1H-indol-1-yl)-4-[(2-{4-[2-
(4-fluorophenoxy)-ethyl]-1-piperidinyl}ethyl)
amino]-3-cyclobutene-1,2-dione and its
methanesulphonate The product is obtained according to the process of
Example 1 using 6-chloroindoline as substrate in Step 1 and
2-{4-[2-(4-fluorophenoxy)ethyl]-1-piperidinyl}ethylamine
as substrate in Step 2.

Melting point: 182–186° C.

EXAMPLE 23

3-[(2-{4-[2-(4-Fluorophenoxy)ethyl]-1-
piperidinyl}ethyl)amino]-4-(5-methoxy-2,3-dihydro-
1H-indol-1-yl)-3-cyclobutene-1,2-dione and its
methanesulphonate The product is obtained according to the process of
Example 1 using 5-methoxyindoline as substrate in Step 1
and 2-{4-[2-(4-fluorophenoxy)ethyl]-1-
piperidinyl}ethylamine as substrate in Step 2.

Melting point: 182–185° C.

EXAMPLE 24

3-[(1-{3-[2-(3,4-Difluorophenyl)ethoxy]propyl}-4-
piperidinyl)amino]-4-(2,3-dihydro-1H-indol-1-yl)-3-
cyclobutene-1,2-dione and its hydrochloride The product is obtained according to the process of
Example 1 using indoline as substrate in Step 1 and 1-{3-
[2-(3,4-difluorophenyl)ethoxy]propyl}-4-piperidineamine
as substrate in Step 2.

Melting point: 250–254° C.

EXAMPLE 25

3-(5Chloro-2,3-dihydro-1H-indol-1-yl)-4-[(2-{4-[2-
(4-fluorophenoxy)-ethyl]-1-piperidinyl}ethyl)
amino]-3-cyclobutene-1,2-dione and its
methanesulphonate The product is obtained according to the process of
Example 1 using 5-chloroindoline as substrate in Step 1 and 2-{4-[2-(4-fluorophenoxy)ethyl]-1-piperidinyl}ethylamine as substrate in Step 2.

Melting point: 167–171° C.

EXAMPLE 26

3-(2,3-Dihydro-1H-indol-1-yl)-4-{[2-[4-{[(4-fluorobenzyl)oxy]methyl}-1-piperidinyl)ethyl]amino}-3-cyclobutene-1,2-dione and its hydrochloride The product is obtained according to the process of Example 1 using indoline as substrate in Step 1 and 2-(4-{[(4-fluorobenzyl)oxy]methyl}-1-piperidinyl)ethanamine as substrate in Step 2.

Melting point: 230–235° C.

EXAMPLE 27

3-(2,3-Dihydro-1H-indol-1-yl)-4-[({1-[2-(1H-indol-3-yl)ethyl]-3-piperidinyl}methyl)amino]-3cyclobutene-1,2-dione and its hydrochloride The product is obtained according to the process of Example 1 using indoline as substrate in Step 1 and {1-[2-(1H-indol-3-yl)ethyl]-3-piperidinyl}methanamine as substrate in Step 2.

Melting point: 237–242° C.

EXAMPLE 28

3-(2,3-Dihydro-1H-indol-1-yl)-4-[({1-[2-(3,4-dimethoxyphenyl)ethyl]-3-piperidinyl}methyl)amino]-3-cyclobutene-1,2-dione and its hydrochloride The product is obtained according to the process of Example 1 using indoline as substrate in Step 1 and {1-[2-(3,4-dimethoxyphenyl)ethyl]-3-piperidinyl}methanamine as substrate in Step 2.

Melting point: 228–232° C.

EXAMPLE 29

3-(5,6-Dimethoxy-2,3-dihydro-1H-indol-1-yl)-4-[(2-{4-[2-(4-fluoro-phenoxy)ethyl]-1-piperidinyl}ethyl)amino]-3-cyclobutene-1,2-dione and its methanesulphonate The product is obtained according to the process of Example 1 using 5,6-dimethoxy-indoline as substrate in Step 1 and 2-{4-[2-(4-fluorophenoxy)ethyl]-1-piperidinyl}-ethylamine as substrate in Step 2.

Melting point: 102–106° C.

EXAMPLE 30

3-({1-[2-(1-Benzofuran-3-yl)ethyl]-4-piperidinyl}amino)-4-(5-methoxy-2,3-dihydro-1H-pyrrolo[2,3-c]pyridin-1-yl)-3-cyclobutene-1,2-dione and its hydrochloride The product is obtained according to the process of Example 1 using 5-methoxy-2,3-dihydro-1H-pyrrolo[2,3-c]pyridine as substrate in Step 1 and 1-[2-(1-benzofuran-3-yl)ethyl]-4-piperidineamine as substrate in Step 2.

Melting point: 278–288° C.

EXAMPLE 31

3-[(2-{4-[2-(4-Fluorophenoxy)ethyl]-1-piperidinyl}ethyl)amino]-4-(4-methoxy-2,3-dihydro-1H-indol-1-yl)-3-cyclobutene-1,2-dione and its methanesulphonate The product is obtained according to the process of Example 1 using 4-methoxyindoline as substrate in Step 1 and 2-{4-[2-(4-fluorophenoxy)ethyl]-1-piperidinyl}ethylamine as substrate in Step 2.

Melting point: 240–244° C.

EXAMPLE 32

3-[(2-{4-[2-(4-Fluorophenoxy)ethyl]-1-piperidinyl}ethyl)amino]-4-(6-methoxy-2,3-dihydro-1H-indol-1-yl)-3-cyclobutene-1,2-dione and its methanesulphonate The product is obtained according to the process of Example 1 using 6-methoxyindoline as substrate in Step 1 and 2-{4-[2-(4-fluorophenoxy)ethyl]-1-piperidinyl}ethylamine as substrate in Step 2.

Melting point: 178–182° C.

EXAMPLE 33

3-(5-Methoxy-2,3-dihydro-1H-pyrrolo[2,3-c]pyridin-1-yl)-4-({2-[4-(2,3,4-trimethoxybenzyl)-1-piperazinyl]ethyl}amino)-3-cyclobutene-1,2-dione and its trihydrochloride The product is obtained according to the process of Example 1 using 5-methoxy-2,3-dihydro-1H-pyrrolo[2,3-c]pyridine as substrate in Step 1 and 2-[4-(2,3,4-trimethoxybenzyl)-1-piperazinyl]ethylamine as substrate in Step 2.

Melting point: 181–183° C.

EXAMPLE 34

3-(5-Methoxy-2,3-dihydro-1H-pyrrolo[2,3-c]pyridin-1-yl)-4-[4-(2,3,4-trimethoxybenzyl)-1-piperazinyl]-3-cyclobutene-1,2-dione and its fumarate The product is obtained according to the process of Example 1 using 5-methoxy-2,3-dihydro-1H-pyrrolo[2,3-c]pyridine as substrate in Step 1 and 4-(2,3,4-trimethoxybenzyl)-1-piperazine as substrate in Step 2.
The product is converted to its fumarate by the action of a solution of fumaric acid.

Melting point: 190–195° C.

EXAMPLE 35

3[(2-{4-[2-(4-Fluorophenoxy)-ethyl]-1-piperidinyl}-ethyl)-amino]-4{[(1-methoxy-cyclobuta[c]pyridin-6-yl)-methyl]-amino}-3-cyclobutene-1,2-dione and its hemifumarate The product is obtained according to the process of Example 1 using 6-aminomethyl-1-methoxy-cyclobuta[c]pyridine as substrate in Step 1 and 2-{4-[2-(4-fluorophenoxy)ethyl]-1-piperidinyl}-ethylamine as substrate in Step 2.
The product is converted to its hemifumarate by the action of a solution of fumaric acid.

Melting point: 190–197° C.

EXAMPLE 36

3-(5-Methoxy-2,3-dihydro-1H-pyrrolo[2,3-c]pyridin-1-yl)-4{2-(spiro[2,3-dihydro-1-benzofurane-3:4'-piperidin-1-yl])-ethyl]-amino}-3-cyclobutene-1,2-dione and its sesquihydrochloride The product is obtained according to the process of Example 1 using 5-methoxy-2,3-dihydro-1H-pyrrolo[2,3-c]

pyridine as substrate in Step 1 and 1-(2-aminoethyl)-spiro[2,3-dihydro-1-benzofurane-3:4'-piperidine] as substrate in Step 2.

The product is converted to its sesquihydrochloride by the action of a solution of chlorhydric acid.

Melting point: 275–280° C.

EXAMPLE 37

3-(4,5-Dimethoxy-2,3-dihydro-1H-indol-1-yl)-4-[(2-{4-[2-(4-fluoro-phenoxy)ethyl]-1-piperidinyl}ethyl)amino]-3-cyclobutene-1,2-dione and its methanesulphonate The product is obtained according to the process of Example 1 using 4,5-dimethoxy-indoline as substrate in Step 1 and 2-{4-[2-(4-fluorophenoxy)ethyl]-1-piperidinyl}-ethylamine as substrate in Step 2.

Melting point: 202–207° C.

EXAMPLE 38

3-(4,5-Dimethoxy-2,3-dihydro-1H-indol-1-yl)$^4$-[(2-{4-(phenoxymethyl)-1-piperidinyl}-ethyl)-amino]-3-cyclobutene-1,2-dione and its methanesulphonate The product is obtained according to the process of Example 1 using 4,5-dimethoxyindoline as substrate in Step 1.

Melting point: 209–213° C.

EXAMPLE 39

3-(4,6-Dimethoxy-2,3-dihydro-1H-indol-1-yl)-4-[(2-{4-[2-(4-fluorophenoxy)]-1-piperidinyl}-ethyl)amino]-3-cyclobutene-1,2-dione and its methanesulphonate The product is obtained according to the process of Example 1 using 4,6-dimethoxyindoline as substrate in Step 1 and 2-{4-[2-(4-fluorophenoxy)ethyl]-1-piperidinyl}-ethylamine as substrate in Step 2.

Melting point 175–180° C.

EXAMPLE 40

3-(4,6-Dimethoxy-2,3-dihydro-1H-indol-1-yl)-4-[(2-{4-(phenoxymethyl)-1-piperidinyl}-ethyl)-amino]-3-cyclobutene-1,2-dione and its methanesulphonate The product is obtained according to the process of Example 1 using 4,6-dimethoxyindoline as substrate in Step 1.

Melting point: 236–240° C.

PHARMACOLOGICAL STUDY OF THE COMPOUNDS OF THE INVENTION

Under standard in vitro conditions, relaxation of aortic rings caused by acetylcholine (ACh), which relaxation is entirely dependent on the presence of endothelium, reflects the production of NO (stimulated by ACh), which, by diffusing to smooth muscle cells, brings about arterial relaxation (*Nature*, 1980, 288, 373).

The compounds of the invention were tested in respect of two models involving two different mechanisms implicated in the endothelial dysfunction observed in pathology:

the first model consists of causing inhibition of the relaxation due to ACh by blocking the enzymatic activity (endothelial NOS) responsible for the production of NO;

the second model consists of causing oxidative stress in vitro using an enzymatic system that generates $O_2^-$(xanthine oxidase —XO and hypoxanthine -Hypo).

EXAMPLE 41

Vascular Protective Effects with Respect to Endothelial Dysfunction Caused by an Inhibitor of NOS The thoracic aorta of a Wistar rat (325–375 g), anaesthetised by the intraperitoneal route using pentobarbital sodium (30 mg/kg), is removed and dissected into rings having a length of 3 mm. Each ring is suspended from an isometric tension sensor connected to a recording system and the initial tension applied is 2.5 g. The physiological solution used, which is thermostatically maintained at 37° C. and oxygenated (95% $O_2$+5% $CO_2$), comprises (in mM): NaCl 112.0; KCl 5.0; $CaCl_2$ 2.5; $KH_2PO_4$ 1.0; $MgSO_4$ 1.2; $NaHCO_3$ 25.0; glucose 11.5; Ca-EDTA 0.016.

After a 90-minute stabilisation period, the preparations are contracted using phenylephrine (PHE $10^{-6}$ M) and relaxed by adding $10^{-5}$ M of acetylcholine in order to verify the integrity of the endothelial layer. If that is confirmed, the preparations are rinsed and a concentration of the test product is added to the medium followed by $3\times10^{-7}$M of $N^G$-nitro-L-arginine (LNA). The preparations are again contracted using phenylephrine and, after 30 minutes, the relaxations due to acetylcholine (ACh-$10^{-8}$M to $10^{-5}$M) are assessed in the presence of indomethacin ($10^{-5}$M).

The relaxation values are expressed as a percentage relative to the maximum contraction caused by PHE. The protective effects of the compounds with respect to the endothelial dysfunction correspond to the difference between the percentages of maximum relaxation observed in the presence or absence of product.

By way of example, the compound of Example 5 at $10^{-7}$M inhibits by 27% the endothelial dysfunction caused by LNA.

EXAMPLE 42

Protective Vascular Effects with Respect to Endothelial Dysfunction Caused by a System Generating $O_2^-$ This protocol, carried out on aortic rings of New Zealand rabbits (2.5–3 kg), is comparable to the previous protocol except for the following points: the initial tension applied is 5 g and the combination XO (3 mU/ml)-Hypo ($10^{-4}$M) is used instead of the LNA.

By way of example, the compound of Example 5 at $10^{-7}$M inhibits by 17% the endothelial dysfunction caused by the XO-Hypo combination.

EXAMPLE 43

Involvement of NO in the Vascular Protective Effects Detected: Assessment of Aortic Production of cGMP By diffusing to smooth muscle cells, the NO produced by the endothelial cells activates soluble guanylate cyclase, which brings about an increase in cyclic GMP, which is responsible for relaxation.

The content of that mediator in rat aortic rings was therefore determined in order to demonstrate that the protective effects of the compounds with respect to endothelial dysfunction are mediated by an increase in the availability of NO.

The rat aortic rings are prepared as previously. The effects of 30-minute incubation of compounds of the invention at different concentrations are assessed on the production of cGMP stimulated by ACh ($10^{-5}$M—1 minute) in the presence of LNA ($3\times10^{-6}$M). The said experiments are carried out in the presence of isobutylmethylxanthine ($10^{-5}$M) in order to avoid degradation of the cGMP by phosphodiesterases. The rings are frozen in liquid nitrogen and maintained at $-80°$ C. until the assay is carried out. The cGMP content is assessed by radioimmunoassay and expressed in relation to the amount of proteins contained in the tissue (assay by the Bradford method).

By way of example, the compound of Example 5, at $3\times10^{-7}$M, increases by 39% the production of cGMP stimulated by ACh in the presence of LNA.

EXAMPLE 44

Pharmaceutical Composition—Tablet

| Formulation for the preparation of 1000 tablets each containing a dose of 10 mg | |
| --- | --- |
| Compound of Example 5 | 10 g |
| Hydroxypropylcellulose | 2 g |
| Polyvinylpyrrolidone | 2 g |
| Wheat starch | 10 g |
| Lactose | 100 g |
| Magnesium stearate | 3 g |

We claim:

1. A compound selected from those of formula (I):

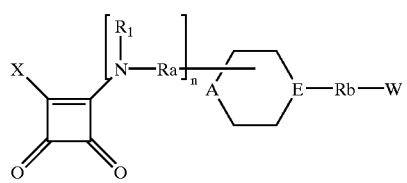

(I)

wherein:

X represents:
   a monocyclic or bicyclic, saturated, partially unsaturated or aromatic heterocycle, having from 5 to 12 ring members, containing from 1 to 3 hetero atoms selected from oxygen, nitrogen and sulphur but containing at least one nitrogen, the heterocycle being bonded to the remainder of the molecule by the nitrogen, and the heterocycle being optionally substituted,
   or a group of formula —$NR_2R_3$ wherein $R_2$ represents hydrogen or linear or branched ($C_1$–$C_6$)alkyl, and $R_3$ represents optionally substituted aryl, 1,3-dihydro-2H-benzimidazolyl-2-one, or linear or branched ($C_1$–$C_6$)alkyl substituted by a monocyclic or bicyclic, saturated, partially unsaturated or aromatic heterocycle, having from 5 to 12 ring members, containing from 1 to 3 hetero atoms selected from oxygen, nitrogen and sulphur but containing at least one nitrogen, the heterocycle being optionally substituted, n represents zero or 1, $R_1$ represents hydrogen or linear or branched ($C_1$–$C_6$) alkyl, Ra represents a single bond or a linear or branched ($C_1$–$C_6$)alkylene chain, A represents nitrogen or CH, it being understood that A represents only CH when Ra "optical isomers" are understood to mean the enantiomers and diastereoisomers.

2. The compound of claim 1, which is selected from those of formula (IA):

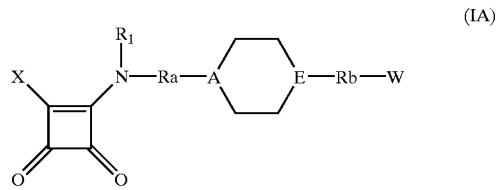

(IA)

wherein X, $R_1$, Ra, A, E, Rb and W are as defined for formula (I).

3. The compound of claim 1, wherein X represents a heterocycle.

4. The compound of claim 1, wherein X represents a group of formula —$NR_2R_3$.

5. The compound of claim 1, wherein X represents a 1-indolinyl group optionally substituted by one or more groups as defined for formula (I).

6. The compound of claim 1, wherein X represents 2,3-dihydro-1H-pyrrolo[2,3-c]pyridin-1-yl optionally substituted by one or more groups as defined for formula (I).

7. The compound of claim 1, wherein X represents a group of formula —$NR_2R_3$ wherein $R_2$ represents hydrogen and $R_3$ represents optionally substituted phenyl.

8. The compound of claim 1, wherein W represents heteroaryl.

9. The compound of claim 1, wherein W represents benzofuryl or indolyl.

10. The compound of claim 1, wherein —Rb—W together represents aryloxyalkyl in which the alkyl moiety has from 1 to 5 carbon atoms and is linear or branched and the aryl moiety is optionally substituted.

11. The compound of claim 1, selected from:
   3-anilino-4-({2-[4-(phenoxymethyl)-1-piperidinyl] ethyl}amino)-3-cyclobutene-1,2-dione and its methanesulphonate,
   3-(4-chloroanilino)-4-({2-[4-(phenoxymethyl)-1-piperidinyl]ethyl}amino)-3-cyclo -butene-1,2-dione and its methanesulphonate,
   3-(2,3-dihydro-1H-indol-1-yl)-4-({2-[4-(phenoxymethyl)-1-piperidinyl]ethyl}amino)-3-cyclobutene-1,2-dione and its methanesulphonate,
   3-({1-[2-(1-benzofuran-3-yl)ethyl]-4-piperidinyl}amino)-4-(4-fluoroanilino)-3-cyclobutene-1,2-dione and its methanesulphonate,
   4-{[2-({1-[2-(1-benzofuran-3-yl)ethyl]-4-piperidinyl}amino)-3,4-dioxo -1-cyclobuten-1-yl] amino}benzonitrile and its methanesulphonate,
   3-[(2-{4-[2-(4-fluorophenoxy)ethyl]-1-piperidinyl}ethyl) amino]-4-[(2-oxo-2,3-dihydro-1H-benzimidazol-5-yl) amino]-3-cyclobutene-1,2-dione and its methanesulphonate
   3-(5-methoxy-2,3-dihydro-1H-pyrrolo[2,3-c]pyridin-1-yl)-4-({2-[4-(phenoxymethyl)-1-piperidinyl] ethyl}amino)-3-cyclobutene-1,2-dione and its dihydrochloride,
   3-[(2-{4-[2-(4-fluorophenoxy)ethyl]-1-piperidinyl}ethyl) amino]-4-(5-methoxy-2,3-dihydro-1H-pyrrolo[2,3-c] pyridin-1-yl)-3-cyclobutene-1,2-dione and its dihydrochloride 3-[(2-{4-[2-(4-fluorophenoxy)ethyl]-1-piperidinyl}ethyl)amino]-4-(4,5,6-trimethoxy-2,3-dihydro-1H-indol-1-yl)-3-cyclobutene-1,2-dione and its methanesulphonate, 3-(6-chloro-2,3-dihydro-1H-indol-1-yl)-4-[(2-{4-[2-(4-fluorophenoxy) -ethyl]-1-piperidinyl}ethyl)amino]-3-cyclobutene-1,2-dione and its methanesulphonate, 3-(2,3-dihydro-1H-indol-1-yl)-4-[({1-[2-(1H-indol-3-yl)ethyl]-3-piperidinyl}methyl)amino]-3-cyclobutene-1,2-dione and its hydrochloride, 3-(5,6-dimethoxy-2,3-dihydro-1H-indol-1-yl)-4-[(2-{4-[2-(4-fluorophenoxy)ethyl]-1-piperidinyl}ethyl)amino]-3-cyclobutene-1,2-dione and its methanesulphonate, 3-[(2-{4-[2-(4-fluorophenoxy)ethyl]-1-piperidinyl}ethyl)amino]-4-(6-methoxy -2,3-dihydro-1H-indol-1-yl)-3-cyclobutene-1,2-dione and its methanesulphonate, and 3-(4,5-dimethoxy-2,3-dihydro-1H-indol-1-yl)-4-[(2-{4-[2-(4-fluorophenoxy)ethyl]-1-piperidinyl}ethyl)amino]-3-cyclobutene-1,2-dione and its methanesulphonate.

12. A pharmaceutical composition comprising as active principle a therapeutically effective amount of a compound as claimed in claim 1, together with one or more inert, non-toxic pharmaceutically acceptable excipients or vehicles.

13. A method of treating the pathogenic and/or aggravating activity of atherosclerosis in a patient in need thereof represents a single bond, and A represents only nitrogen when n represents zero, E represents nitrogen or CRe wherein Re represents either hydrogen, or a bond to a carbon atom of W, it being understood that A and E cannot both represent nitrogen at the same time.

Rb represents a single bond or a linear or branched $(C_1-C_6)$alkylene chain, one of the carbon atoms of which is optionally replaced by oxygen or sulphur, W represents aryl or heteroaryl, each of those groups being optionally substituted, its optical isomers, its hydrates, its solvates and addition salts thereof with a pharmaceutically acceptable acid, it being understood that:

"aryl" is selected from phenyl, biphenyl, bicyclo[4.2.0]octa-1,3,5-trienyl, naphthyl, dihydronaphthyl, tetrahydronaphthyl, indanyl and indenyl, "heteroaryl" is an aryl group as defined above containing from 1 to 3 identical or different hetero atoms selected from oxygen, nitrogen and sulphur, "optionally substituted", when associated with "heterocycle", "aryl" or "heteroaryl", is understood to mean optionally substituted by one or more identical or different groups selected from halogen, linear or branched $(C_1-C_6)$alkyl, hydroxy, linear or branched $(C_1-C_6)$alkoxy, mercapto, linear or branched $(C_1-C_6)$alkylthio, linear or branched $(C_1-C_6)$trihaloalkyl, cyano, nitro, amino, linear or branched $(C_1-C_6)$-alkylamino, dialkylamino in which each alkyl moiety has from 1 to 6 carbon atoms and is linear or branched, and methylenedioxy, comprising the step of administering to the living body a therapeutically effective amount of a compound of claim 1.

14. The method of claim 13, wherein the pathogenic and/or aggravating activity of atherosclerosis is the prevention of atheroma formation.

15. The method of claim 13, wherein the pathogenic and/or aggravating activity of atherosclerosis is the prevention of development of atherosclerotic lesions.

16. The method of claim 13, wherein the pathogenic and/or aggravating activity of atherosclerosis is the prevention or treatment of spasm, thrombosis, restinosis or accelerated atherosclerosis in patients undergoing myocardial by-pass, transplant, arterial dilatation with or without stent, or repermeabilization.

* * * * *

UNITED STATES PATENT AND TRADEMARK OFFICE
CERTIFICATE OF CORRECTION

PATENT NO. : 6,696,469 B2
DATED : February 24, 2004
INVENTOR(S) : Jean-Louis Peglion et al.

It is certified that error appears in the above-identified patent and that said Letters Patent is hereby corrected as shown below:

Title page,
Item [56], References Cited, OTHER PUBLICATIONS, "DeFily" reference, "Preconditioning protects coromary endothelium" should be -- Preconditioning protects coronary arteriolar endothelium --.

Column 15,
Line 31, Claim 1 should read:
-- A compound selected from those of formula (I):

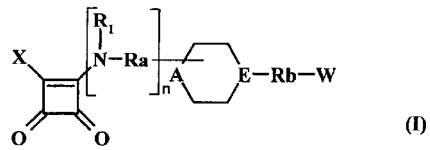

wherein:
X represents:
- a monocyclic or bicyclic, saturated, partially unsaturated or aromatic heterocycle, having from 5 to 12 ring members, containing from 1 to 3 hetero atoms selected from oxygen, nitrogen and sulphur but containing at least one nitrogen, the heterocycle being bonded to the remainder of the molecule by the nitrogen, and the heterocycle being optionally substituted,
- or a group of formula $-NR_2R_3$ wherein $R_2$ represents hydrogen or linear or branched $(C_1-C_6)$alkyl, and $R_3$ represents optionally substituted aryl, 1,3-dihydro-2H-benzimidazolyl-2-one, or linear or branched $(C_1-C_6)$alkyl substituted by a monocyclic or bicyclic, saturated, partially unsaturated or aromatic heterocycle, having from 5 to 12 ring members, containing from 1 to 3 hetero atoms selected from oxygen, nitrogen and sulphur but containing at least one nitrogen, the heterocycle being optionally substituted,

UNITED STATES PATENT AND TRADEMARK OFFICE
CERTIFICATE OF CORRECTION

PATENT NO. : 6,696,469 B2
DATED : February 24, 2004
INVENTOR(S) : Jean-Louis Peglion et al.

It is certified that error appears in the above-identified patent and that said Letters Patent is hereby corrected as shown below:

<u>Column 15 (cont'd),</u>
n represents zero or 1,

Signed and Sealed this

Twenty-fourth Day of August, 2004

JON W. DUDAS
*Director of the United States Patent and Trademark Office*

UNITED STATES PATENT AND TRADEMARK OFFICE
CERTIFICATE OF CORRECTION

PATENT NO.    : 6,696,469 B2
DATED         : February 24, 2004
INVENTOR(S)   : Jean-Louis Peglion et al.

It is certified that error appears in the above-identified patent and that said Letters Patent is hereby corrected as shown below:

Title page,
Item [56], References Cited, OTHER PUBLICATIONS, "DeFily" reference,
"Preconditioning protects coromary endothelium" should be -- Preconditioning protects coronary arteriolar endothelium --.

Column 15,
Line 31, Claim 1 should read:
-- A compound selected from those of formula (I):

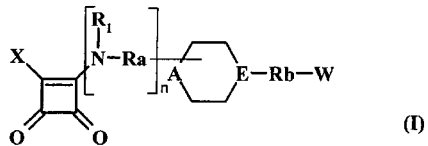

(I)

wherein:
X   represents:
- a monocyclic or bicyclic, saturated, partially unsaturated or aromatic heterocycle, having from 5 to 12 ring members, containing from 1 to 3 hetero atoms selected from oxygen, nitrogen and sulphur but containing at least one nitrogen, the heterocycle being bonded to the remainder of the molecule by the nitrogen, and the heterocycle being optionally substituted,
- or a group of formula $-NR_2R_3$ wherein $R_2$ represents hydrogen or linear or branched $(C_1-C_6)$alkyl, and $R_3$ represents optionally substituted aryl, 1,3-dihydro-2H-benzimidazolyl-2-one, or linear or branched $(C_1-C_6)$alkyl substituted by a monocyclic or bicyclic, saturated, partially unsaturated or aromatic heterocycle, having from 5 to 12 ring members, containing from 1 to 3 hetero atoms selected from oxygen, nitrogen and sulphur but containing at least one nitrogen, the heterocycle being optionally substituted, n     represents zero or 1, $R_1$  represents hydrogen or linear or branched $(C_1-C_6)$alkyl, Ra    represents a single bond or a linear or branched $(C_1-C_6)$alkylene chain, A     represents nitrogen or CH, it being understood that A represents only CH when Ra represents a single bond, and A represents only nitrogen when n represents zero, E     represents nitrogen or CRe wherein Re represents either hydrogen, or a bond to a carbon atom of W, it being understood that A and E cannot both represent nitrogen at the same time, Rb    represents a single bond or a linear or branched $(C_1-C_6)$alkylene chain, one of the carbon atoms of which is optionally replaced by oxygen or sulphur,

UNITED STATES PATENT AND TRADEMARK OFFICE
CERTIFICATE OF CORRECTION

PATENT NO. : 6,696,469 B2
DATED : February 24, 2004
INVENTOR(S) : Jean-Louis Peglion et al.

It is certified that error appears in the above-identified patent and that said Letters Patent is hereby corrected as shown below:

Column 15 (cont'd),

W represents aryl or heteroaryl, each of those groups being optionally substituted, its optical isomers, its hydrates, its solvates and addition salts thereof with a pharmaceutically acceptable acid, it being understood that :
- "aryl" is selected from phenyl, biphenyl, bicyclo[4.2.0]octa-1,3,5-trienyl, naphthyl, dihydronaphthyl, tetrahydronaphthyl, indanyl and indenyl,
  "heteroaryl" is an aryl group as defined above containing from 1 to 3 identical or different hetero atoms selected from oxygen, nitrogen and sulphur, "optionally substituted", when associated with "heterocycle", "aryl" or "heteroaryl", is understood to mean optionally substituted by one or more identical or different groups selected from halogen, linear or branched ($C_1$-$C_6$)alkyl, hydroxy, linear or branched ($C_1$-$C_6$)alkoxy, mercapto, linear or branched ($C_1$-$C_6$)alkylthio, linear or branched ($C_1$-$C_6$)trihaloalkyl, cyano, nitro, amino, linear or branched ($C_1$-$C_6$)-alkylamino, dialkylamino in which each alkyl moiety has from 1 to 6 carbon atoms and is linear or branched, and methylenedioxy,
  "optical isomers" are understood to mean the enantiomers and diastereoisomers.

Column 17,
Line 28, claim 13, should read:

" A method of treating the pathogenic and/or aggravating activity of atherosclerosis in a patient in need thereof, comprising the step of administering to the living body therapeutically effective amount of a compound of claim 1."

This certificate supersedes Certificate of Correction issued August 24, 2004.

Signed and Sealed this

Nineteenth Day of October, 2004

JON W. DUDAS
*Director of the United States Patent and Trademark Office*